US012623001B2

(12) United States Patent
Agreli et al.

(10) Patent No.: US 12,623,001 B2
(45) Date of Patent: May 12, 2026

(54) AORTIC STENT

(71) Applicant: CV Cardiovascular GmbH, Vienna (AT)

(72) Inventors: Guilherme Agreli, Sao Jose de Rio Preto (BR); Katharina Kiss, Vienna (AT); Siegfried Einhellig, Munich (DE)

(73) Assignee: CV Cardiovascular GmbH, Vienna (AT)

( * ) Notice: Subject to any disclaimer, the term of this patent is extended or adjusted under 35 U.S.C. 154(b) by 0 days.

(21) Appl. No.: 17/588,790

(22) Filed: Jan. 31, 2022

(65) Prior Publication Data

US 2022/0257834 A1 Aug. 18, 2022

(30) Foreign Application Priority Data

Feb. 18, 2021 (EP) .................................... 21157884

(51) Int. Cl.
| | |
|---|---|
| *A61L 27/36* | (2006.01) |
| *A61F 2/24* | (2006.01) |
| *A61L 27/50* | (2006.01) |

(52) U.S. Cl.
CPC ........ *A61L 27/3625* (2013.01); *A61F 2/2409* (2013.01); *A61F 2/2418* (2013.01);
(Continued)

(58) Field of Classification Search
CPC ............. A61L 27/3625; A61L 27/3641; A61L 27/3687; A61L 27/50; A61L 2400/02;
(Continued)

(56) References Cited

U.S. PATENT DOCUMENTS

| | | | |
|---|---|---|---|
| 5,413,798 A | 5/1995 | Scholl et al. | |
| 2003/0014105 A1* | 1/2003 | Cao ....................... | A61F 2/2409 |
| | | | 623/2.15 |

(Continued)

FOREIGN PATENT DOCUMENTS

| | | | | |
|---|---|---|---|---|
| EP | 3693030 A1 | 8/2020 | | |
| KR | 20060112332 A | * 11/2006 | ............. | A61L 27/38 |
| WO | 2011160085 A2 | 12/2011 | | |

OTHER PUBLICATIONS

European Patent Office. Extended European Search Report for EP Application No. 21157884.4, mailed Aug. 10, 2021, pp. 1-3.
(Continued)

*Primary Examiner* — Sarah W Aleman
*Assistant Examiner* — Rebecca Lynee Zimmerman
(74) *Attorney, Agent, or Firm* — Vivacqua Crane, PLLC

(57) ABSTRACT

The invention relates to a stent for placement at an aortic annulus that is expandable from an undeployed state to a deployed state comprising a stent frame having rows of cells with a proximal section and a distal section at a longitudinal axis of the stent, the stent frame being formed by a plurality of arms, the arms being connected to one another at connection points, and wherein the plurality of arms forms a plurality of diamond-shaped stent cells, in particular the rows of cells, formed of vertices at said connection points between the arms, a dry valve made out bovine pericardium arranged at least at the distal section of the stent with the dry bovine pericardium being configured to be rehydrated with a solution, a skirt surrounding the dry valve and comprising at least one of bovine pericardium and polyester, and one or more eyelets arranged at a distal end of some of the arms, with the eyelets being configured to fix the valve to the stent frame.

17 Claims, 4 Drawing Sheets

(52) U.S. Cl.

CPC ....... *A61L 27/3641* (2013.01); *A61L 27/3687* (2013.01); *A61L 27/50* (2013.01); *A61F 2220/0025* (2013.01); *A61L 2400/02* (2013.01); *A61L 2430/20* (2013.01)

(58) Field of Classification Search

CPC ............... A61L 2430/20; A61L 31/005; A61L 2430/40; A61F 2/2409; A61F 2/2418; A61F 2220/0025; A61F 2250/0039; A61F 2/2415; A61F 2/90; A61F 2/2412; A61F 2/2442; A61F 2/2466; A61F 2/958; A61F 2/966; A61F 2/97; A61F 2220/0008; A61F 2230/0017

See application file for complete search history.

(56) References Cited

U.S. PATENT DOCUMENTS

| | | | |
|---|---|---|---|
| 2008/0077234 A1* | 3/2008 | Styrc | A61F 2/2409 |
| | | | 623/2.11 |
| 2008/0102439 A1 | 5/2008 | Tian et al. | |
| 2009/0180965 A1 | 7/2009 | Freyman et al. | |
| 2010/0004740 A1* | 1/2010 | Seguin | A61F 2/2418 |
| | | | 623/2.18 |
| 2010/0185277 A1* | 7/2010 | Braido | A61F 2/2433 |
| | | | 623/2.37 |
| 2011/0301700 A1 | 12/2011 | Fish et al. | |
| 2012/0071969 A1* | 3/2012 | Li | A61F 2/2412 |
| | | | 623/2.17 |
| 2016/0095701 A1* | 4/2016 | Dale | A61F 2/2412 |
| | | | 623/2.18 |
| 2016/0166381 A1* | 6/2016 | Sugimoto | A61L 31/022 |
| | | | 623/2.11 |
| 2017/0112620 A1* | 4/2017 | Curley | A61F 2/2418 |
| 2017/0325945 A1* | 11/2017 | Dale | A61F 2/2418 |
| 2019/0001023 A1 | 1/2019 | Ashworth et al. | |
| 2019/0358036 A1 | 11/2019 | Cooper et al. | |
| 2020/0069415 A1* | 3/2020 | Bialas | A61F 2/243 |
| 2020/0214834 A1 | 7/2020 | Rzany et al. | |
| 2020/0368178 A1* | 11/2020 | Naso | A61K 31/353 |
| 2020/0405478 A1* | 12/2020 | Millwee | A61F 2/2418 |
| 2021/0038380 A1* | 2/2021 | Tabor | A61F 2/013 |
| 2022/0072202 A1 | 3/2022 | Kiss et al. | |
| 2022/0175522 A1* | 6/2022 | Salahieh | A61F 2/2418 |
| 2023/0077632 A1* | 3/2023 | Wang | A61L 27/3625 |
| | | | 435/378 |

OTHER PUBLICATIONS

Mori, S., et al. "A New Decalcifying Technique for Immunohistochemical Studies of Calcified Tissue, Especially Applicable to Cell Surface Marker Demonstration," Journal of Histochemistry and Cytochemistry, vol. 36, No. 1, 1988, pp. 111-114.

\* cited by examiner

AORTIC STENT

CROSS REFERENCE TO RELATED APPLICATIONS

This application claims the benefit of foreign priority under 35 U.S.C. § 119 of European patent application number 21157884.4, filed Feb. 18, 2021. The contents of this application are incorporated herein by reference in their entirety.

INTRODUCTION

The present invention relates to a stent for placement at an aortic annulus that is expandable from an undeployed state to a deployed state.

A healthy heart facilitates oxygenated blood flow to the extremities. The heart is comprised of two chambers: the right chamber and the left chamber, which manage deoxygenated and oxygenated blood respectively. Deoxygenated blood from the upper and the lower extremities, travels through both caval veins, i.e. the vena cava superior and the vena cava inferior, into the right atrium. It is pumped through the tricuspid valve and into the right ventricle. During systole, when the ventricle is full, the tricuspid valve shuts and blood is pumped from the right ventricle through the pulmonary valve into the pulmonary artery and to the lungs where it is oxygenated. Following said oxygenation, blood is pumped back to the left side of the heart, i. e. the left atrium, through the pulmonary vein. As the atrium contracts, oxygenated blood flows from the left atrium through the mitral valve into the left ventricle. During systole, when the left ventricle is full, the left ventricle ejects the blood through the aortic valve into the aorta and to the rest of the body as well as to the coronary arteries which supply the heart muscle itself.

A native aortic valve is one of the two semilunar valves of the heart and consists of three leaflets that are attached directly to the wall of the annulus. There are three cusps in the native aortic valve: the left coronary cusp (LCC), right coronary cusp (RCC), and the non-coronary cusp (NCC). The bellies of these cusps define the annulus of the native aortic valve. The annulus is predominantly circular or elliptical in shape. At the location of the cusp attachment, the aortic anatomy is typically at its largest diameter, and this defines the sinus region. The sinus of the aortic anatomy is critical to the healthy functioning of the heart as the coronary arteries, which carry oxygenated blood to the heart muscles, originate here.

In patients with aortic stenosis, the integrity of the native leaflets and the annulus is compromised primarily due to calcification. A compromised valvular apparatus prevents the leaflets from fully opening during systole, thus affecting the hemodynamic functioning of the valve. In instances where this condition persists for an extended period of time, the left ventricle remodels to compensate, affecting cardiac performance and patient health.

Surgical aortic valve replacement offers physicians the greatest flexibility regarding implant type—with choices of either a mechanical or bioprosthetic heart valve. The decision of whether an operation is possible is based on many factors, including age, surgeon preference, patient tolerance to blood thinners, and comorbidities. Surgical replacement is recommended for patients who are a low or intermediate surgical risk. Elderly patients who are at a high surgical risk or inoperable due to comorbidities require a different alternative.

One drawback of existing technologies is leakage around the valve, termed paravalvular leakage (PVL). PVL is usually a result of at least one of the following malpositioning of an implant, calcium interference with implant expansion, incorrect sizing of the implant and/or implant migration.

Therefore, biological tissues are widely used to make prosthetic replacements for heart valves and blood vessels as well as for transcatheter heart valves. They are connective tissues comprising collagen as the main component. Among these tissues, bovine pericardium is one of the most widely employed. Pericardial tissue is the sac surrounding the heart which provides a natural barrier to infection for the heart and prevents adhesion to the surrounding tissue. The pericardium also serves mechanical roles, for example, by preventing over dilation of the heart, maintaining the correct anatomical position of the heart, and regulating the pressure to volume ratio in the left ventricle during diastole. The structure of the tissue determines its behavior under loading in both conditions physiologic to the pericardium and as a prosthetic device.

However, biological tissues obtained from the abattoir, in particular porcine and bovine cadavers, begin to degrade immediately. Therefore, the storage of such materials has proven to be difficult. For this purpose, a biological tissue, such as e.g. bovine or porcine pericardium or a heart valve, is usually chemically treated to improve its mechanical performance and immunogenic properties, reduce thrombogenicity and degradation, preserve sterility, and prolong the allowable storage period.

Accordingly, biological tissues are known which can be used as bioprosthetic devices that can be stored dry before used for clinical applications. Additionally, special care has to be taken in connection with the preparation methods in order to avoid the formation of degenerative calcific deposits. Calcification, in particular pathologic calcification, of soft biological tissues due to deposition of calcium phosphate mineral salts in an implanted tissue is undesirable and the deposition of the calcific deposits can have severe consequences on device performance. Calcification of implants can lead to stiffening, structural instability and ultimately to device failure.

Although there are difficulties in the usage of biological tissues, their performance inside a human body has proven to be significantly better.

SUMMARY

For this reason, it is an object of the present invention to make available a stent by means of which PVL is prevented as far as possible and with which trauma during surgery can be reduced, so that the stent can also be used with elderly patients. This object is solved by the subject matter of independent claim 1.

Such a stent for placement at an aortic annulus is expandable from an undeployed state to a deployed state. The stent comprises a stent frame having rows of cells and a proximal section and a distal section at a longitudinal axis of the stent. The stent frame is formed by a plurality of arms, the arms being connected to one another at connection points. The plurality of arms further forms a plurality of diamond-shaped stent cells, in particular the rows of cells, formed of vertices at said connection points between the arms. Furthermore, the stent comprises a dry valve made out bovine pericardium arranged at least at the distal section of the stent with the dry bovine pericardium being configured to be rehydrated with a solution. Also, a skirt surrounding the dry valve and comprising at least one of bovine pericardium and polyester is provided. Additionally, the stent comprises one or more eyelets arranged at a distal end of some of the arms, with the eyelets being configured to fix the valve to the stent frame.

The stent for an implant or prosthesis described herein is in particular suitable for the treatment of aortic stenosis via minimally invasive transcatheter implantation to replace a defective aortic valve.

The stent comprises a plurality of arms which build the stent frame with two sections, i.e. the proximal section and the distal section. The expansion of the stent is made possible by the plurality of arms that are interconnected in such a way that following the expansion they adapt to the anatomical need of the location of the stent. In this way the design of such a stent is adapted to accommodate the anatomical needs and implantation locations. The stent furthermore consists of an expandable, in particular a balloon-expandable, stent frame. Moreover, between 6 and 50 arms can be provided to form the stent frame.

Therefore, the plurality of arms is connected to one another at connection points and form a plurality of diamond-shaped stent cells, in particular the rows of the stent cells, formed of vertices at said connection points between the arms. In this connection it should be noted that the term vertex refers to a corner region of each cell, i.e. the region of the cell forming a corner where two respective sections of the arms meet. Preferably the vertex at least substantially forms an origin of the corner where two respective sections of the arms meet.

It should further be noted in this connection that the sections of the plurality of arms forming sides of the stent cells are linear, such that the formed stent cells comprise a diamond shape. Such shapes can be manufactured in a simple manner and provide the stent frame with an increased stability and flexibility.

Due to the short length of the stent, the implant comprising such a stent can be placed more accurately within a blood vessel thereby improving the function of the implant due to the increased apposition to the native annular anatomy using appropriate design options. This is necessary to reduce trauma to a patient during implantation, and to ensure accurate implant placement. The reduction of trauma to a patient also makes the surgery less critical so that this kind of implant can also be provided in patients who were previously not operable due to the too high a risk associated with the implantation of prior art designs.

The stent comprises a dry valve made of bovine pericardium, which upon final placement at the aortic artery can be rehydrated with a solution such as a saline solution. Hence, a pericardium as an animal biological tissue material is used, in particular obtained from a bovine heart that may have been treated with a crosslinking agent. The natural human heart valve, which is supposed to be fixed with the invention, is identified as the aortic valve. Therefore, the pericardium is used to replace the damaged or diseased naturally occurring heart valve. Also, such a valve can allow the pre-loading of the stent within a delivery system.

The valves are made using bovine pericardium. The ECM (Extracellular Matrix) tissue is generally harvested from the pericardial sac of cows and is then used to manufacture the leaflets. The tissue from pericardial sac is particularly well suited for a valve leaflet due to its durable physical properties. The tissues are glutaraldehyde fixed, non-viable, chemically treated (decellularized) and sterilized so that the biological markers are removed making them more compatible with the patient's immune system.

The potential benefits of bovine pericardium are superior biocompatibility, demonstrates minimal suture line bleeding and patency can be immediately confirmed by ultrasound, such as TEE ultrasound. They also have benefits like lack of calcification, support of cellular ingrowth and reduced rates of restenosis and infection. The pericardium is durable, strong and available in various sizes.

In order to seal the stent once put in place, the stent further comprises a skirt, which surrounds the dry valve at. The skirt therefore provides sealing between the stent and the right ventricle of the heart. Said skirt comprises at least one of bovine pericardium and polyester, preferably of both of said materials.

To assist the fixation of the valve to the heart the valve may further have a PET fabric skirt that attaches the tissue to the stent frame. PET material is highly inert and does not create any adverse reaction in human body. The PET material also permits ingrowth of cells into the cloth which helps hold the valve in place minimizing thrombosis at the same time.

Generally speaking PTFE suture lines may be used for fixation on fixing the stent to the heart.

Furthermore, the stent comprises one or more eyelets arranged at a distal end of some of the arms, with the eyelets being configured to fix the valve to the stent frame. Hence, said eyelets can be used to, for example, suture the valve to the stent frame in order to fix the valve permanently to the stent frame. The eyelets are located at the distal end of the stent in order to provide the suture lines at a position of the stent farther away from the native valve which is supposed to be repaired/replaced.

In this connection it is noted that it may not be necessary to attach the valve at each arm of the frame. The exact amount of attachment points, i.e. eyelets, may be chosen as needed.

Also, as already mentioned above, the stent can be divided into at least two sections, i.e. the proximal section and the distal section, which are arranged adjacent to each other at a longitudinal axis. The lengths, sizes and dimensions of the respective sections are believed to be particularly suitable for a minimally invasive treatment of aortic artery diseases. Selecting the length appropriately may enable an interference fit between the stent and the aortic artery to be sufficient to prevent the stent from becoming dislodged in time.

According to an embodiment of the invention two eyelets are provided at each one of said arms of said some of the arms. In this connection it is noted that it might not be necessary to provide eyelets at each arm of the stent frame. In some applications it may sufficient to provide eyelets at every second arm or maybe only at two or three arms. The exact number of arms comprising eyelets may be chosen according to the precise application or according to the exact anatomical conditions of the patient. By providing two eyelets at each one of said arms, which is supposed to comprise eyelets, the suturing of the valve to the stent frame is made easier and more reliable since there are more openings given at each arm at which the valve can be fixed.

The dry valve may comprise between two and six leaflets, preferably three or four leaflets, with the leaflets being connected to the stent frame at said eyelets. It has shown that for stents shaped circularly in the region of attachment of the valve, a valve comprising three leaflets is the best option in order to distribute the forces of the blood flow present in the heart evenly during the opening and closing process of the valve. Nevertheless, the exact number of leaflets may be chosen according to the application, the medical condition, the anatomical properties of the patient and so on.

In this connection it is noted that the eyelets for fixing the valve at the stent frame may be arranged at the point where two adjacent leaflets of the valve meet. Hence, for a valve comprising three leaflets, the stent may comprise three arms having eyelets, which are arranged at the said meeting point. This way, two leaflets can be fixed at the same arm.

According to another embodiment the stent comprises four rows of cells along the longitudinal axis. Depending on the size of the cells the number of rows may differ. Furthermore, depending on the patient the number of rows and/or the sizes of the cells may differ. Thus, for an adult patient the stent may generally be chosen to be bigger than for a child, for example.

Common sizes for the areas of the stent cells, in the expanded state, lie in the range of 25 to 200 $mm^2$, in particular in the range of 35 to 120 $mm^2$. Therefore, a total amount of four rows of cells has proven to be advantageous for most adult patients.

The dry bovine pericardium may have a maximum tensile stress selected in the range of 20 to 25 MPa, and/or wherein the rehydrated bovine pericardium has a tensile stress selected in the range of 12 to 15 MPa. Thus, the dry bovine pericardium can comprise a tensile resistance which can be up to 15 times higher than the tensile resistance of the leaflets of a human heart. This is mainly done for safety reasons in order to minimize tearing or fracture of the pericardium.

The mechanical properties of a material, in particular tensile strength, can be tested under strain-stress evaluation using Universal Testing Machine (Oswaldo Filizzola, model AME-2 kN).

Also, the dry bovine pericardium may have a calcium content selected in the range of 0.01 to 0.1 g/Kg. The bovine leaflets may generally be as flexible and durable similar to the patient's natural tissue and therefor individual with such replacement valve may not require blood thinner medication on a continuous basis. Bovine pericardium tissue provide better hemodynamics in view of their similarity to natural flexible leaflet valves, some bovine pericardium valves may have some limitation on durability due to calcification and degeneration process. Treating the valves with a specialized anti-calcification treatment makes them more resistant to calcification. The valves having such a calcium content are hence more resistant to calcification and are more durable.

According to another embodiment of the invention the dry bovine pericardium is formed using a method of treatment comprising the following steps:

(1) soaking of the bovine pericardium treated with a crosslinking agent with a saline solution;

(2) contacting the soaked bovine pericardium with an aqueous solution comprising Hydrogen Peroxide;

(3) contacting the bovine pericardium with an aqueous solution comprising PBS and EDTA;

(4) contacting the bovine pericardium with a solution comprising glycerol, ethanol and EDTA; and (5) contacting the bovine pericardium with a glycerol solution.

One embodiment of the present invention utilizes soaking of the bovine pericardium treated with a crosslinking agent with a saline solution.

As used herein, a crosslinking agent is glutaraldehyde which is preferably used in biochemical and medicine applications as an amine-reactive homobifunctional cross-linker. As already mentioned above, glutaraldehyde treatment produces stable cross-links in cellular and extracellular matrix proteins which substantially reduced graft immunogenicity. However, such tissue has altered mechanical property, early mechanical failure, cytotoxicity, and incomplete suppression of immunological recognition. Besides this severe calcification was noticed in glutaraldehyde-treated bovine pericardium. An emerging alternative to glutaraldehyde treatment is further treatment according to the method steps, i.e. a method allowing to reduce calcification of the bovine pericardium.

It is preferably to use the crosslinking agent in an amount of from 0.1% to 5.0% by volume, more preferably from 0.2% to 3.0% by volume, further preferably from 0.3% to 2.0% by volume and especially preferably from 0.5% to 1.0% by volume.

In this respect, as a first step a soaking of the bovine pericardium with an aqueous saline solution comprising 0.9% of sodium chloride (9.0 g per litre) is carried out. Such a solution is also commonly named as normal saline, physiological saline or isotonic saline solution.

In a second step, the soaked bovine pericardium is contacted with an aqueous solution comprising Hydrogen Peroxide. It is preferred that the concentration of hydrogen peroxide is from 0.05% by volume to 5.0% by volume, preferably from 0.1% by volume to 3.0% by volume, more preferably from 0.2% by volume to 2.0% by volume.

In a third step of the present invention, the bovine pericardium is contacted with an aqueous solution comprising PBS and EDTA.

As used herein, the term "contacting" means treating, immersion, exposing to, rinsing of the biological tissue used in the inventive method.

As used herein, the term "PBS" is directed to a phosphate buffered saline having a pH of 7.4 and containing water based salt solution of disodium hydrogen phosphate, sodium chloride and, in some formulations, potassium chloride and potassium dihydrogen phosphate. PBS is used in biological and medical applications, such as washing cells, transportation of tissues and dilutions, because PBS closely mimics the pH, osmolarity, and ion concentrations of the human body.

The term "aqueous solution" refers to a solution comprising a substance or a compound and water that has been purified to remove contaminants which are able to influence the end product. Preferably, distilled water, double distilled water or deionized water is used in a method of the present invention.

The term "EDTA" is used herein to refer to ethylenediaminetetraacetic acid which is a complexing chelating agent being able to sequester metal ions especially like $Fe^{2+}/Fe^{3+}$, $Al^{3+}$, $Mg^{2+}$, $Ca^{2+}$, $Mn^{2+}$, $Zn^{2+}$ and others and to remove them from the solution forming so called EDTA-complexes.

According to embodiment, it is especially important to remove calcium ions from the solution by forming calcium chelator that has been shown to inhibit mineralization of biological tissues, in particular bovine pericardium tissue. It is suggested that EDTA binds to calcium ions on the outer shell of hydroxyapatite crystals which are formed from calcium phosphate crystals thereby chelating and removing calcium ions from the crystals, causing the tissue material to shrink thus demineralizing the material.

Treatment of biological tissues with EDTA hence slows down the progression of calcification by binding calcium before it can react to form hydroxyapatite. Since the calcification of biological tissues used e.g. as bioprosthetic heart valves is a clinically significant problem that contributes to implant failure, it is of significant importance to reduce calcium level in biological tissues used as an implant.

Therefore in the present invention, the EDTA treatment can reduce calcium level in biological tissues, especially in bovine or porcine pericardium or a heart valve preferably by 20%, more preferably by 30%, further preferably by 40% and especially preferably by 50%. Further, it is preferable to use EDTA in combination with PBS in order to increase demineralization and compatibility with a human body.

Furthermore, it is preferable to use EDTA, in particular in steps (3) and (4), having a concentration of more than 0.01% by weight, preferably of more than 0.05% by weight, more preferably of more than 0.10% by weight, still preferably of more than 0.15% by weight, and of less than 10.0% by weight, preferably of less than 8.0% by weight, more preferably of less than 6.0% by weight, still preferably of less than 5.0% by weight, further preferably of less than 3.0% by weight. Still further in the present invention, it is preferably to use disodium EDTA.

In a fourth step of the present invention, the bovine pericardium is contacted with a solution comprising glycerol, ethanol and EDTA, and in a fifth step the bovine pericardium is contacted with a glycerol solution in order to further reduce calcification of biological tissue and to dehydrate the bovine pericardium. The following steps describe an implementation of these processes in the method.

After the bovine pericardium has been processed through steps (1) to (3) of the method, they undergo the treatment in a solution comprising glycerol, ethanol and EDTA.

Phospholipids in and around biological tissue cells have been found the most prominent calcification nucleation sites. Therefore, the removal of these tissue components has been proposed to reduce mineralization, in particular calcification. Different studies have shown these to be effective calcification prevention strategies. The organic solvents like ethanol or glycerol or a mixture of ethanol and glycerol can be similarly used for this purpose. For example, the treatment with at least 70% ethanol, preferably with at least 80% ethanol, more preferably with at least 90% ethanol, extracts phospholipids from the tissue while also causing a change in collagen conformation that increases bioprosthesis resistance to collagenase. Thus, ethanol treatment allows extracting almost all phospholipids and cholesterols from the bioprosthesis, thus eliminating calcification of the biological tissue cells. Additionally, ethanol treatment also prevents adsorption of phospholipids and cholesterols from the solution. The method by which glycerol fixes biological tissue is not jet fully understood, but a 98% concentration, preferably 99% concentration, is sufficient to treat the biological tissue to make the tissue more biocompatible and resistant to calcification.

In this respect, it is preferably to treat biological tissue in a solution comprising glycerol, ethanol and EDTA for at least 60 minutes, preferably for at least 75 minutes, more preferably for at least 90 minutes, at room temperature, in particular at a temperature of 10° C. to 25° C., preferably at a temperature of 15° C. to 25° C., more preferably at a temperature of 18° C. to 22° C., under stirring of not more than 500 rpm, preferably of not more than 300 rpm, more preferably of not more than 50 rpm. During this time most of the water molecules presented in biological tissue, in particular pericardial tissue, are replaced with glycerol.

Furthermore, it is preferable to use a mixture of glycerol and ethanol, wherein a volume ratio of glycerol to ethanol is preferably from 1:5 to 5:1, more preferably from 1:4 to 4:1, still preferably from 1:3 to 3:1, further preferably from 1:2 to 2:1.

The bovine pericardium is then removed from the solution and placed in glycerol for further dehydration for at least 60 minutes, preferably for at least 75 minutes, more preferably for at least 90 minutes, at room temperature, in particular at a temperature of 10° C. to 25° C., preferably at a temperature of 15° C. to 25° C., more preferably at a temperature of 18° C. to 22° C., under stirring of not more than 500 rpm, preferably of not more than 300 rpm, more preferably of not more than 50 rpm.

It can further be preferable to use an additional step of contacting or rinsing the bovine pericardium with ethanol having a concentration of at least 70% by volume, preferably with at least 80% by volume, more preferably with at least 90% by volume. The additional step, in particular step (3a), is preferably carried out before contacting the biological tissue with a solution comprising glycerol, ethanol and EDTA. It can further be preferable to carry out another additional step (5a) of contacting the biological tissue with ethanol after the step of contacting the biological tissue with a glycerol and before the step of drying the biological tissue. It can still further be preferable to carry out an additional step (3a) and/or (5a) using a mixture of ethanol and EDTA having a concentration as in step (3) or (4).

The bovine pericardium is removed from the solution and exposed to ambient air or an inert environment, e.g. nitrogen, at room temperature and humidity so as not to adversely affect tissue properties. Preferably, the drying is performed in a clean room at ambient conditions for at least 12 hours, preferably for at least 16 hours, still preferably for at least 20 hours. Further preferably, the drying is performed under high efficiency particulate air (HEPA) filter, in particular under HEPA conditions in a clean room. As used herein, the term "ambient conditions" is directed to the ambient temperature of more than 10° C., preferably of more than 12° C., more preferably of more than 14° C., especially preferably of more than 18° C., and preferably of less than 25° C., more preferably of less than 23° C., further preferably of less than 22° C. Further in the present invention it is preferably to carry out each of steps (1) to (7) at the ambient conditions as described above.

The treated and dried bovine pericardium is then packaged in a container or package essentially free of liquid for subsequent surgical implantation. As used herein, the term "essentially free of liquid" means a non-fluid environment in which the presence of water or other substances is limited to approximately the content of such substances in ambient air.

In another embodiment of the invention the skirt is arranged to cover the stent frame at least a part of the distal section and/or a part of the proximal section, preferably the whole stent, from within. The skirt may cover at least the region, which is occupied by the valve. Usually, in order to provide a better sealing, a length of the skirt is longer than a length of the valve. In some embodiments the skirt may even cover the whole stent from within.

Once in place, the skirt will be pressed against the stent frame due to blood flow through the valve from the proximal to the distal end. Depending on the precise anatomy of the patient, the stents may comprise different sizes and thus also different skirt sizes. For some cases it may be better to have a longer skirt, which covers most parts of the stent while in other cases a short skirt, which covers only the distal section and small parts of the proximal section, may be sufficient.

Hence, it may also be possible that the skirt covers the above mentioned four rows of cells completely. In another embodiment the skirt may cover only three rows while leaving some of the cells of the most distal row out. As can be seen, the exact length as well as the number of cells covered by the skirt can be chosen freely.

In an embodiment all ends of the arms at the distal and the proximal section lie in a common plane to avoid having single arms that may poke the artery or the ventricle.

The eyelets of the distal end may project beyond said common plane at the ends of the arms, especially wherein the eyelets lie in a further common plane, in particular ends of the eyelets remote from the ends of the arms lie in said further common plane.

The stent further may also comprise means for attaching the stent at the distal and/or a proximal end of the stent frame such that it can be ensured that the stent remains at its intended place. Such means can, for example, be further eyelets arranged at the ends of the arms. Said eyelets can either lie in the common plane spanned by the ends of the arms or can project beyond said plane. In the second case, the eyelets can lie in a common plane as well which may overlap with the common plane of the eyelets used for fixing the valve to the stent frame.

The stent frame may be made out of at least one of chromium, cobalt and Nitinol. Nitinol is a collapsible and flexible metal, which is furthermore self-expandable and comprises a shape-memory. Hence, the frame can automatically self-expand to an outer shape, which can be chosen beforehand since Nitinol can memorize said chosen shape. Chromium and cobalt, on the other hand, have proven to be advantageous material when using balloon extendable stents since they are a high tensile metallic alloy which does not show a recoil or spring effect. Furthermore, said materials comprise a good corrosion resistance and biocompatibility and can show a permanent plastic deformation.

A diameter of the distal section and the proximal section may be larger than a diameter of a middle section arranged between the distal section and the proximal section. Hence, it can be seen that the stent can be divided in three parts. The lengths, sizes and dimensions of the respective parts are believed to chosen to be particularly suitable for a minimally invasive treatments of conditions that require urgent intervention. One of said shapes may be the shape of a nucleus of a torus.

Such a stent aims to increase the effective orifice area, i.e. the area inside the valve, and to create an optimal indication for valve-in-valve application in small annulus bioprosthesis or bicuspid heavy calcified aortic valves.

In this connection it should be noted that the stent frame may have a shape that corresponds to or at least substantially corresponds to the shape of a nucleus of a torus, i.e. of the inner part of the torus surrounding the central aperture of the torus. Such a stent frame increases the effective orifice area, i. e. the area inside the valve. Since said area depends on the radius of the stent, the area obviously increases when the leaflets are attached at an area of the stent which comprises a bigger radius. The radius of the middle part of the stent is usually limited by the size of the aortic annulus or the bioprosthetic ring.

To achieve a bigger area inside the valve, the suture of leaflets at the stent frame is arranged at the distal end of the stent, where the diameter of the stent may be larger (as mentioned above). In this case, the area inside the valve is not decreased by the suture restriction.

A radius of curvature between the proximal section, the middle section and the distal section may lie in the range of 5 to 50 mm, preferably 10 to 40 mm, in particular 20 to 30 mm.

According to a second aspect of the invention a delivery device for delivering a self-expandable stent according to the invention, the delivery device comprising a flush port, a main body part for holding, inflating and/or releasing the stent, and an actuation mechanism for moving the stent to a delivery site.

The device may be preloaded with a stent so that this can be stored ready to use on a shelf in a medical facility to significantly reduce the treatment time of acute aortic syndromes leading to reduced mortality rates of acute aortic syndromes.

The actuation mechanism may have a torque control and may be able to rotate the stent about an axis of the main body. In this way the stent can be positioned in relation to the extremities in an as good as possible manner at the aortic valve, to deploy the valve and stent at the desired delivery site. The device may further be improved with steerable control, to increase precision and accuracy at deployment.

Also, the device may have a knob or the like at the actuation mechanism, with the knob in particular being able to be rotated about an axis of rotation of the actuation mechanism. By turning the knob the lumen is able to deflect and allows a better positioning of the tip and the main body of the delivery device and less stress over the system during deployment. This leads to an improved accuracy of deployment of the delivery device and hence of a stent that is delivered to a delivery site using the delivery device.

BRIEF DESCRIPTION OF THE DRAWINGS

The invention will be described in detail by means of embodiments and with reference to the drawings. These show preferred embodiments. The features described may be configured in various combinations, which are encompassed in this document. The drawings show.

DETAILED DESCRIPTION

Figure 1:
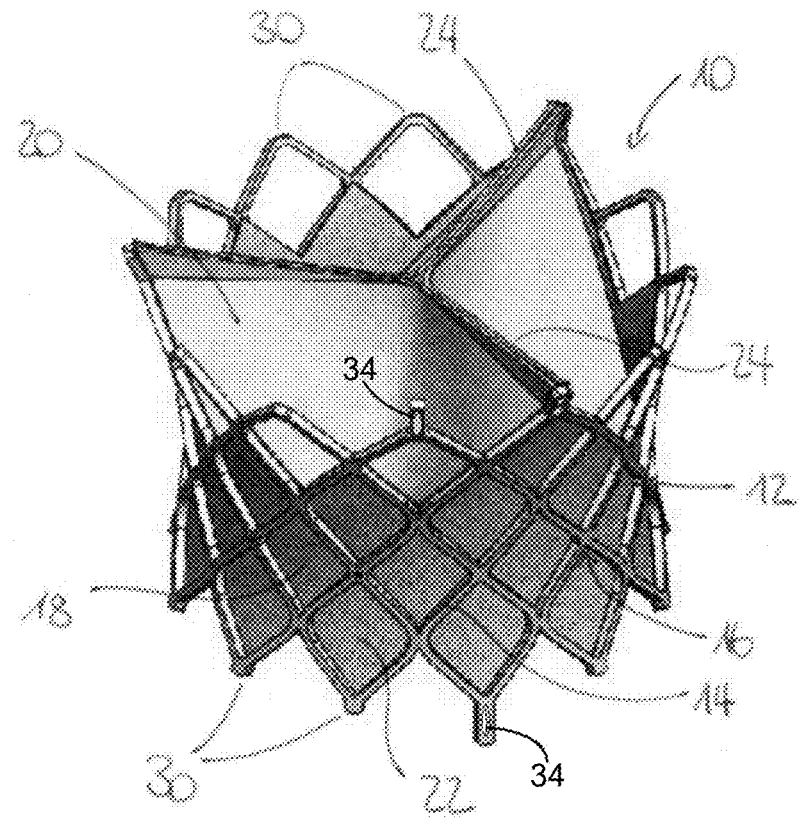
FIG. 1: a perspective view of an aortic stent.

FIG. 1 shows a perspective view of a stent 10 according to the invention with a stent frame 12 composed of a plurality of arms 14. The stent 10 can be a balloon-expandable or a self-expandable stent 10, both configured to be placed at the aortic artery and the aortic valve of a patient. The stent frame 12 can be composed of Chromium and Cobalt, in the case of a balloon-expandable stent 10, or Nitinol if a self-expandable stent 10 is desired. Both versions of the stent 10 can be delivered in a compressed state to a point of interest such as the aortic artery of a human, where it then can be (self-)expanded once it is deployed.

The frame 12 further comprises at least two sections, i.e. a proximal section PS and a distal section DS, arranged at a longitudinal axis A. Often the stent further comprises a third section, i.e. a middle section MS, which is arranged between the proximal section PS and the distal section DS respectively. All sections DS, MS, PS are interconnected with each other. In this connection it is noted that the terms "distal" and "proximal" refer to said end of the stent which is farther away or closer to the heart of the patient, respectively, once the stent 10 is put in place.

The frame 12 is further characterized in that the arms 14 are connected one to another at a plurality of connection points 16 such that they form a web-like structure of diamond-shaped cells 18. In the embodiment of FIG. 1 the stent 10 is composed of four rows of cells 18 arranged along the longitudinal axis A of the stent 10. Generally, the stent 10 can also comprise more or less rows of cells 18 depending on the application, the anatomical conditions of the patient etc.

Each stent cell 18 in the present example is formed of four sides and four vertices. The four sides of the stent cells 18 are respectively formed by sections of the arms 14 and the vertices are either formed by an end of an arm 14 or a connection point 16.

Figure 4:
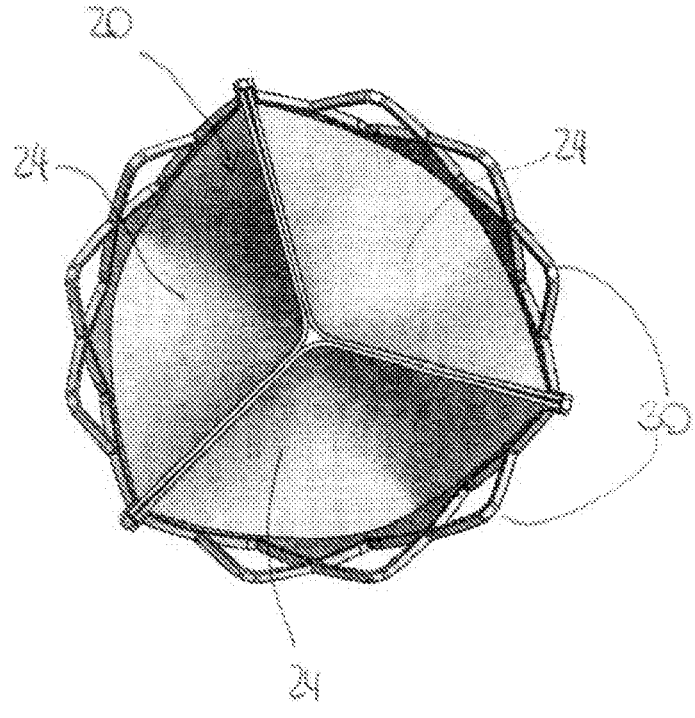
FIG. 4: a top view of the stent of FIG. 1.

The distal section DS of the stent 10 further comprises a valve 20 made out of dry bovine pericardium as well as a skirt 22 made out of dry bovine pericardium and polyester. The valve 20 comprises three leaflets 24 which are attached to the stent frame 12 at eyelets 26 arranged at some arms 14 at a distal end DE of the frame 12 (FIG. 1 and FIG. 4). In the depicted embodiment three arms 14—corresponding to the three leaflets 24—are provided with eyelets 26, wherein each one of said arms 14 comprises two eyelets 26 to which the leaflets 26 can be attached to, i.e. sutured, i.e. an eyelet is provided per leaflet. As one can also see, said eyelets 26 are provided at the position where two adjacent leaflets 24 meet such that both of said leaflets 24 can be sutured to one arm 14.

The eyelets 26 are arranged such that they are positioned at apexes between two directly adjacent leaflets 26, with the region of the respective leaflets at the apexes being fixed to the eyelets in order to stabilize the dry valve 20 in this region to ensure a correct functioning, i.e. opening and closing, of the leaflets 26 even in the region of the apexes.

Figure 3:
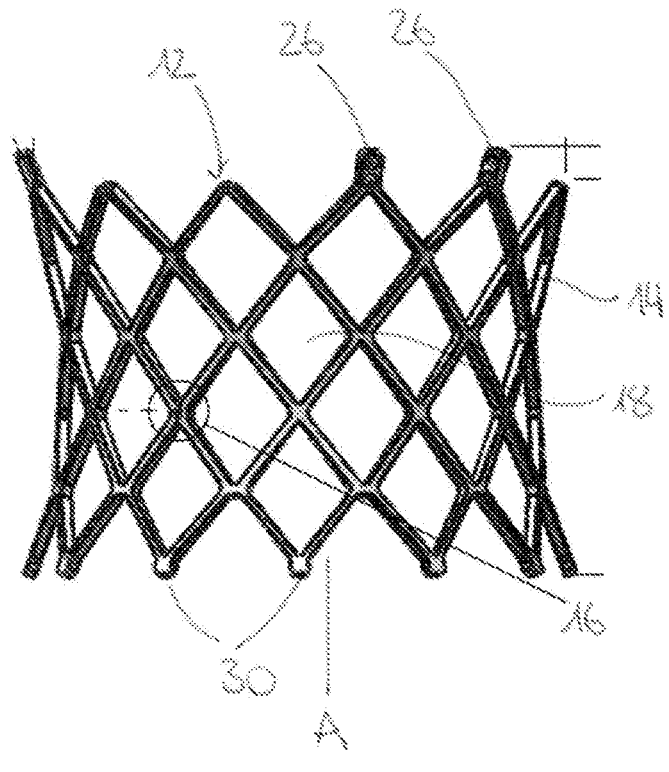
FIG. 3: a side view of a stent frame.

Generally speaking, also every arm 14 could be provided with eyelets 26. The exact number of arms 14 which will be provided with eyelets 26 may be chosen according to the application. For example, if a valve 20 with only two leaflets 24 is chosen to be placed inside the stent 10, only two arms 14 may be provided with eyelets 26. In some embodiments, on the other hand, the eyelets 26 can always be provided at two adjacent arms 14 in order to fix two adjacent leaflets 24 to the stent frame 12 (see FIG. 3).

Figure 5:
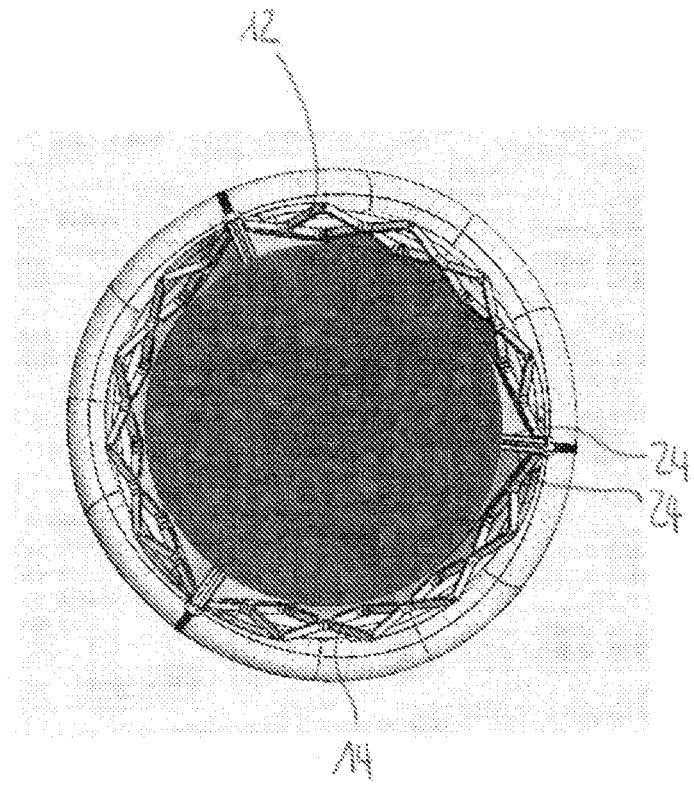
FIG. 5: a top view of a stent including a native artery and a marked inner space.

The eyelets 26 are provided at the distal end DE of the stent 10 in order to maximize the area inside the stent, especially at the middle section MS (see FIG. 5). By placing the eyelets 26 at the distal end DE the suturing does not decrease the effective area inside the stent 10.

Figure 2:
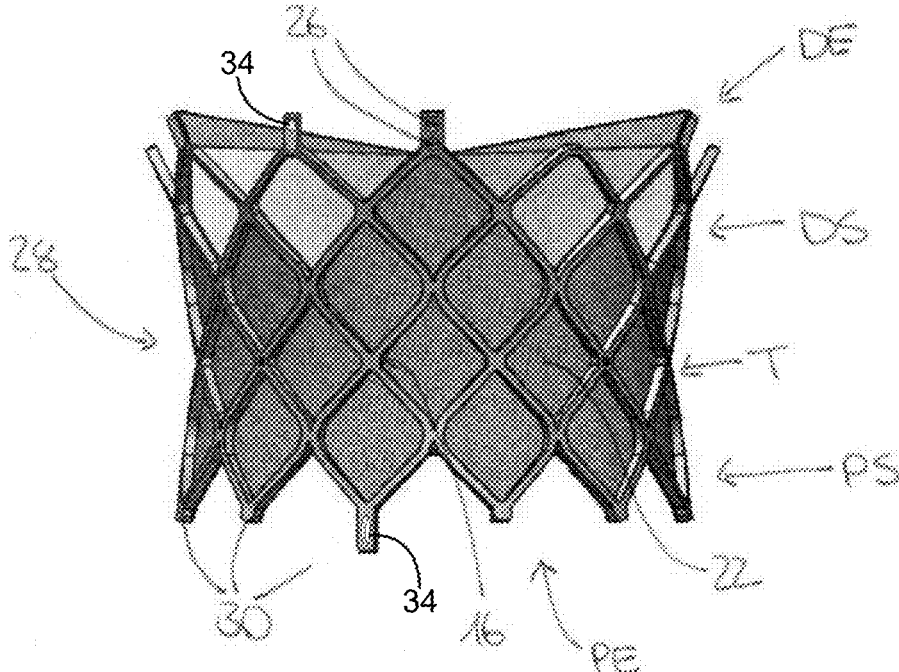
FIG. 2: a side view of the aortic stent of FIG. 1.

Due to anatomical reasons of the aortic artery and of the right ventricle of the heart, the skirt 22 does not only surround the valve 20 at the distal section DS but may cover up to 100% of the stent 10 to prevent leakage between the stent 10 and the ventricle of the patient's heart (see FIG. 2). In the embodiment of FIG. 2, for example, three out of four rows of cells 18 are covered by the skirt 22. Only some of the cells 18 of the last row at the distal end DE of the stent 10, namely the ones which are right underneath the eyelets 26 are provided with a skirt 22.

An outer contour of the stent 10 of FIGS. 1 to 5 can be described as having the following shapes, an approximately cylindrical shape in both the proximal section PS and the distal section DS with the distal end DE and a proximal end PE both having a slightly convex outer surface 28. Starting from the proximal end PE the proximal section PS then transitions into the middle section MS which then transitions into the distal section DS. The respective transitions T correspond to a mathematical turning point such that the outer surface 28 of the stent comprises a radius of curvature which lies in the range of 20 to 30 mm.

Hence, a maximum outer diameter of both the distal and the proximal section DS, PS is larger than a maximum outer diameter of the middle section MS. Preferably the maximum outer diameters of the distal and the proximal sections are the same. In some cases it may nevertheless be advantageous to provide with different diameters, such as a bigger diameter for the distal section DS than for the proximal section PS. The middle section MS comprises the smallest diameter in order to avoid compression of the coronary arteries, which wrap the whole heart, can be prevented.

Generally speaking the outer contour is selected to adapt to the shape of the blood vessel into which it is fitted with the distal section PS being adapted to create a tight interference fit with the blood vessel to ensure that the positioning of the stent 10 does not vary in time. The proximal section is designed to have an interference fit with the aorta superior to the aortic annulus. This interference fit may add minor, but additional, stability to the valve 20 once positioned.

In order to be able to attach the stent 10 at its respective point of interest, i.e. the aortic artery, the stent 10 can comprise further eyelets 34 at its respective proximal and/or distal ends PE, DE. That is, after being expanded, the stent 10 does not only hold itself in place by into the aortic artery but also by being sutured. This way, it may also be possible to attach the proximal end PE of the stent 10 at the transition of the aortic artery and the right ventricle of the heart or at the wall of the right ventricle itself such that the stent 10 protrudes inside the ventricle. The exact attachment point and technique can thus be chosen according to the different conditions at the different hearts which are being treated with the invention.

The ends 30 of the arms 14 at both ends of the stent 10 can lie in a common plane. The eyelets, which are used to attach the stent to the artery 34 can comprise a rectangular outer shape with a rectangular opening for suturing the stent 10 to the aortic artery. Generally, said eyelets can also comprise a different shape, e. g. a circular shape, for both the outer and the inner shape. The eyelets 26 as well as the eyelets for suturing the stent 10 to the artery can project beyond said common plane of the ends 30 of the arms 14 and span another common plane.

Figure 6:
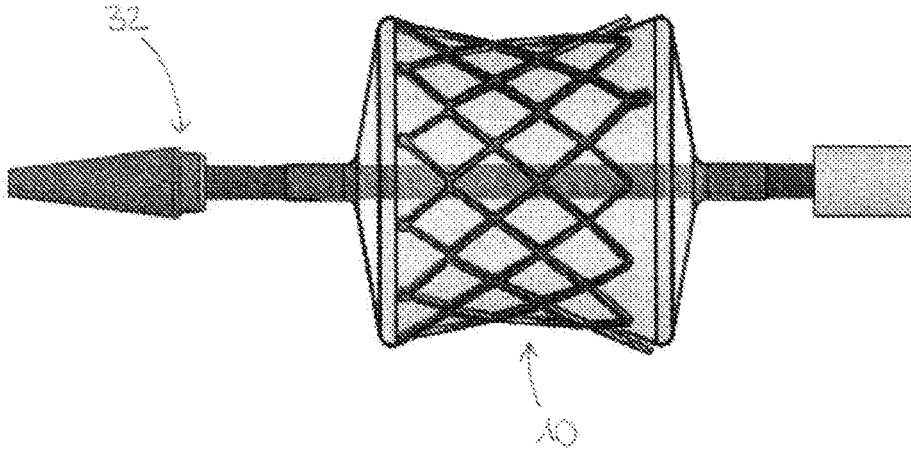
FIG. 6: a part of a delivery device delivering the stent.

FIG. 6 shows a delivery device 32 for delivering the (balloon-) expandable stent 10 also known as catheter. Such a delivery device can be configured to inflate a balloon which then expands the stent once it is put in place. Such delivery devices are common state of the art and are thus not described in detail.

Figure 7:
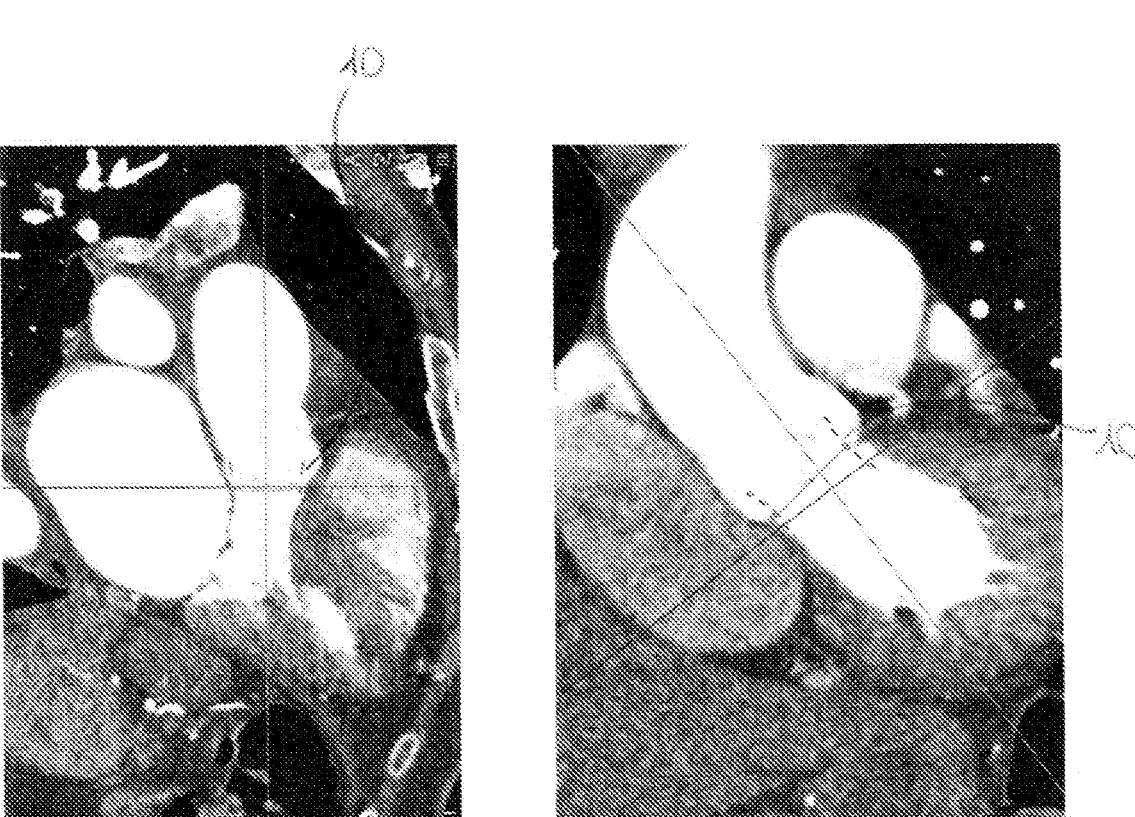
FIG. 7: CT pictures of a delivered stent.
Figure 8:
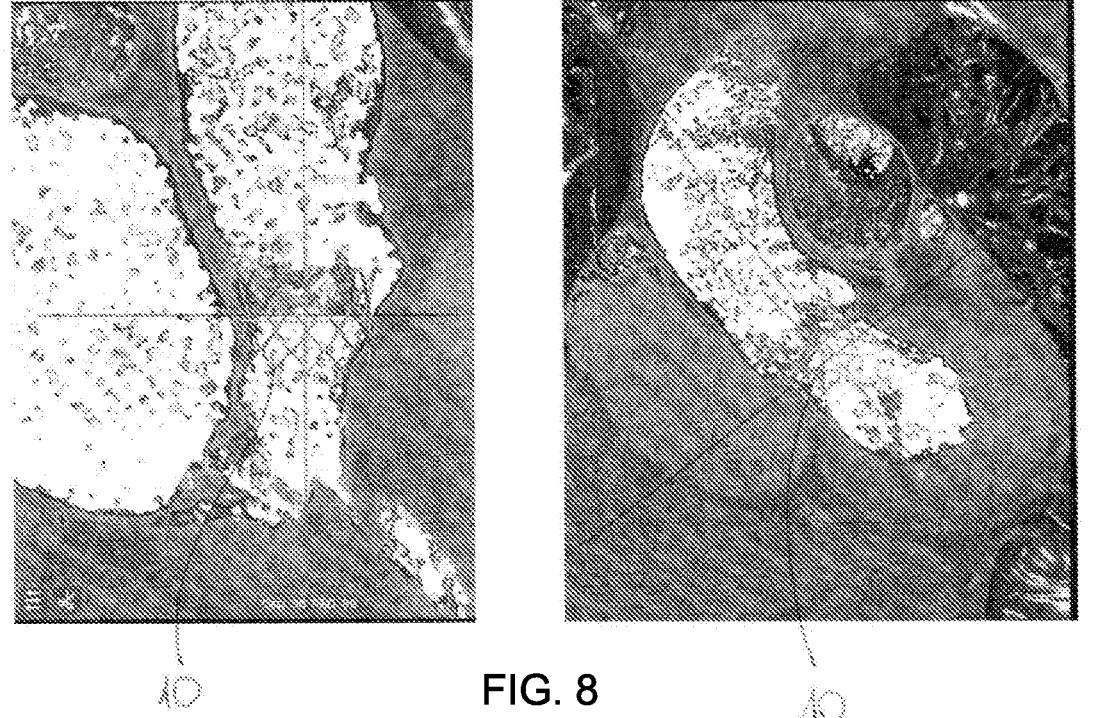
FIG. 8: CT pictures of the delivered stent of FIG. 7.

In FIGS. 7 and 8 one can see different MRI pictures of a stent 10, which has been deployed at the aortic artery of a patient, preferably using the delivery device 32 of FIG. 6. The different pictures in FIGS. 7 and 8 show the same stent 10 from different angles. As one can see in those CT pictures, the stent 10 is in the expanded state and has been deployed at the transition between the aortic artery and the right ventricle of the patient.

REFERENCE LISTING

10 stent
12 frame
14 arms
16 connection point
18 cell
20 valve
22 skirt
24 leaflet 13
14

26 eyelet
28 outer surface
30 end of arms
32 delivery device
A longitudinal axis
DE distal end
DS distal section
MS middle section
PE proximal end
PS proximal section
T transition

What is claimed is:

1. A stent for placement at an aortic annulus that is expandable from an undeployed state to a deployed state, the stent comprising:

a stent frame having rows of cells with a proximal section and a distal section at a longitudinal axis of the stent, wherein a diameter of the distal section and the proximal section is larger than a diameter of a middle section arranged between the distal section and the proximal section, the stent frame being formed by a plurality of arms, the plurality of arms being connected to one another at connection points, and wherein the plurality of arms forms a plurality of diamond-shaped stent cells, in particular the rows of cells, formed of vertices at said connection points between the plurality of arms, and wherein the stent frame has a shape that corresponds to the shape of a nucleus of a torus, a dry valve made out of bovine pericardium arranged at least at the distal section of the stent with the dry bovine pericardium being configured to be rehydrated with a solution, wherein the dry bovine pericardium has a maximum tensile stress selected in a range of 20 to 25 MPa, wherein the rehydrated bovine pericardium has a tensile stress selected in a range of 12 to 15 MPa, and wherein the dry bovine pericardium is formed using a method of treatment comprising the steps of:

(1) soaking the bovine pericardium treated with a crosslinking agent with a saline solution, (2) subsequent to step (1), contacting the bovine pericardium with an aqueous solution comprising Hydrogen Peroxide, (3) subsequent to step (2), contacting the bovine pericardium with an aqueous solution comprising PBS and EDTA, (4) subsequent to step (3), contacting the bovine pericardium with a solution comprising glycerol, ethanol and EDTA, and (5) subsequent to step (4), contacting the bovine pericardium with a glycerol solution, a skirt surrounding the dry valve and comprising at least one of bovine pericardium and polyester, two or more eyelets arranged at a distal end of at least one of the arms, wherein the dry valve is fixed to the at least one of the arms by connection to each of the two or more eyelets.

2. The stent in accordance with claim 1, wherein the dry valve comprises between two and six leaflets, with the leaflets being connected to the stent frame at said two or more eyelets.

3. The stent according to claim 1, wherein the stent comprises four rows of cells along the longitudinal axis.

4. The stent in accordance with claim 1, wherein the dry bovine pericardium has a calcium content selected in a range of 0.01 to 0.1 g/Kg.

5. The stent according to claim 1, wherein the skirt is arranged to cover at least the distal section of the stent frame from within.

6. The stent according to claim 1, wherein the skirt is arranged to cover at least the proximal section of the stent frame from within.

7. The stent according to claim 1, wherein the skirt is arranged to cover the whole stent from within.

8. The stent according to claim 1, wherein all ends of the plurality of arms at the distal and the proximal section lie in a common plane.

9. The stent according to claim 8, wherein the two or more eyelets of the distal end project beyond said common plane at the ends of the plurality of arms.

10. The stent according to claim 9, wherein the two or more eyelets lie in a further common plane.

11. The stent according to claim 10, wherein ends of the two or more eyelets remote from the ends of the plurality of arms lie in said further common plane.

12. The stent according to claim 1, wherein the stent further comprises one or more artery attachment eyelets for attaching the stent frame to an artery at at least one of the distal end and a proximal end of the stent frame.

13. The stent according to claim 12, wherein the one or more artery attachment eyelets for attaching the stent frame to an artery are configured to be attached to an aortic artery.

14. The stent according to claim 1, wherein the stent frame is made out of at least one of chromium, cobalt and Nitinol.

15. The stent according to claim 1, wherein a radius of curvature between the proximal section, the middle section and the distal section lies in a range of 5 to 50 mm.

16. The stent according to claim 1, wherein a radius of curvature between the proximal section, the middle section and the distal section lies in a range of 10 to 40 mm.

17. The stent according to claim 1, wherein a radius of curvature between the proximal section, the middle section and the distal section lies in a range of 20 to 30 mm.

* * * * *